United States Patent
Yin et al.

(10) Patent No.: US 9,079,839 B2
(45) Date of Patent: Jul. 14, 2015

(54) METHODS FOR PREPARATION OF PHARMACEUTICAL INTERMEDIATES OF ALISKIREN

(76) Inventors: Xuezhi Yin, Jiangsu (CN); Bing Wang, Jiangsu (CN); Ying Ji, Jiangsu (CN); Mingyuan Liu, Jiangsu (CN)

( * ) Notice: Subject to any disclaimer, the term of this patent is extended or adjusted under 35 U.S.C. 154(b) by 245 days.

(21) Appl. No.: 13/884,408

(22) PCT Filed: Jun. 16, 2011

(86) PCT No.: PCT/CN2011/075800
§ 371 (c)(1),
(2), (4) Date: May 9, 2013

(87) PCT Pub. No.: WO2012/062109
PCT Pub. Date: May 18, 2012

(65) Prior Publication Data
US 2013/0231509 A1    Sep. 5, 2013

(30) Foreign Application Priority Data

Nov. 9, 2010   (CN) .......................... 2010 1 0535822

(51) Int. Cl.
*C07C 41/22*    (2006.01)
(52) U.S. Cl.
CPC ..................................... *C07C 41/22* (2013.01)
(58) Field of Classification Search
CPC ....................................................... C07C 41/22
USPC ................................................. 568/649, 663
See application file for complete search history.

(56) References Cited

U.S. PATENT DOCUMENTS 5,559,111 A    9/1996 Goschke et al.

FOREIGN PATENT DOCUMENTS

CN    102001920 A    4/2011

OTHER PUBLICATIONS

Disclosed Anonymously; "Process for Preparation of (2S, 4S, 5S, 7S)-5-amino-N-(2-carbamoyl-2-methyl-propyl)-4-hydroxy-7-{[4-methoxy-3-(3-Methoxypropoxy) pheyl] methyl}-8-methyl-2-propan-2-yl-nonanamide and Intermediates thereof", IP.com, Inc. IP.com No. IPCOM000181980D; IP.com Electronic Publication: Apr. 21, 2009, 31 pages.
Richard Göschke, et al; "The Nonchiral Bislactim Diethoxy Ether as a Highly Stereo-Inducing Synthon for Sterically Hindered, γ-Branched α-Amino Acids: A Practical, Large-Scale Route to an Intermediate of the Novel Renin Inhibitor Aliskiren", Helvetica Chimica Acta, vol. 86, Issue 8, pp. 2848-2870 Published Aug. 2003.
Hua Dong, et al; "Practical synthesis of an orally active rennin inhibitor aliskiren", Tetrahedron Letters, vol. 46, pp. 6337-6340; Available online Jul. 28, 2005.

*Primary Examiner* — Rosalynd Keys
(74) *Attorney, Agent, or Firm* — Flener IP Law; Zareefa B. Flener

(57) ABSTRACT

Disclosed are methods for preparation of two pharmaceutical intermediates (I, II) of Aliskiren, said intermediates are obtained by reacting compound of formula I or II and tribromophosphorus oxide. The method replaces the method in the prior art which is using column chromatopraphy to produce the compounds I and II, and overcomes the defect that the method in the prior art hardly carry out in a large-scale industrial production. The product can be purified by recrystallization or vacuum distillation, and the chemical purity of the product is good.

14 Claims, No Drawings

METHODS FOR PREPARATION OF PHARMACEUTICAL INTERMEDIATES OF ALISKIREN

FIELD OF THE INVENTION

The present invention relates to the field of medicine, in particular to a method for preparation of intermediates of an antihypertensive agent—Aliskiren.

BACKGROUND OF THE INVENTION

Cardiovascular diseases, including hypertension, are the No. 1 lethal factor in the world, and are known as the "First Killer against Human Health". At present, anti-hypertensive drugs available in the market are mainly divided into the following categories: diuretics (thiazide drugs), β-receptor blockers (-lol drugs), calcium antagonists (dipine drugs), angiotensin converting enzyme (ACE) inhibitors (pril drugs), Angiotensin II-receptor antagonists (sartan drugs). Among patients with hypertension, only 25% cases can be controlled with existing drugs. Aliskiren is the first non-peptide renin inhibitor approved by FDA in 2007, which attains vasodilation and blood pressure lowering effects by inhibiting renin activity and thereby decreasing the levels of angiotensin I and angiotensin II. A unique feature of Aliskiren is: it can inhibit plasma renin activity (PRA), which not only is a risk factor for myocardial infarction of patients with hypertension, but also is closely related with target organ damage. Decreasing PRA is helpful for protection of the target organ. That feature is an important feature that differentiates renin inhibitor drugs from other antihypertensive drugs.

Aliskiren was originally developed by Novartis, the chemical compound patent is U.S. Pat. No. 5,559,111A, and the synthetic route is shown as follows:

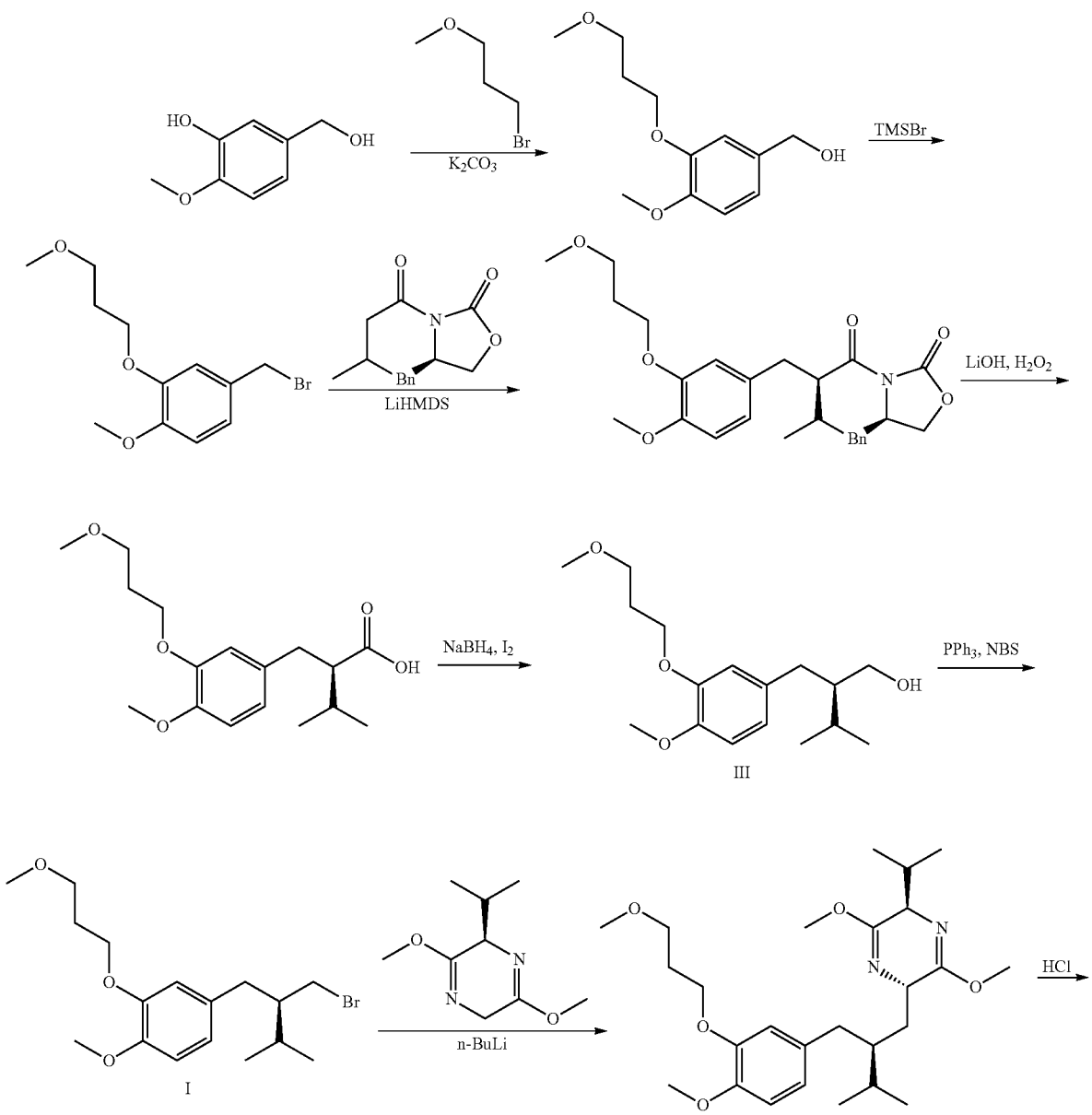

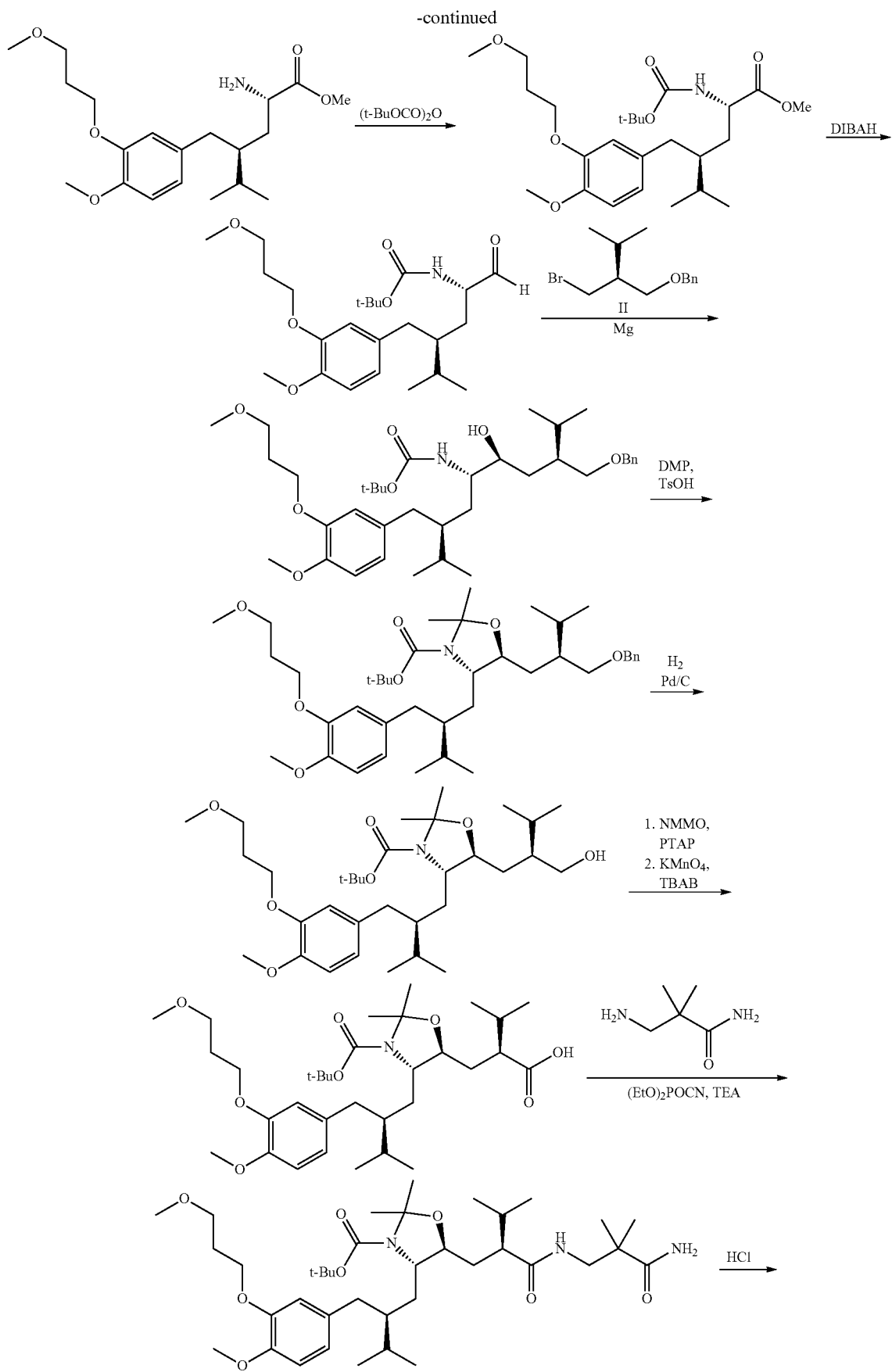

-continued

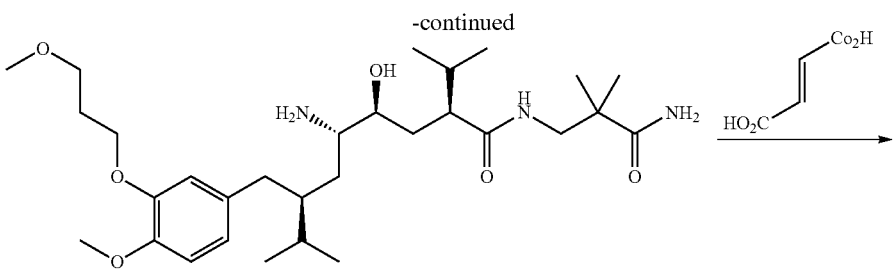

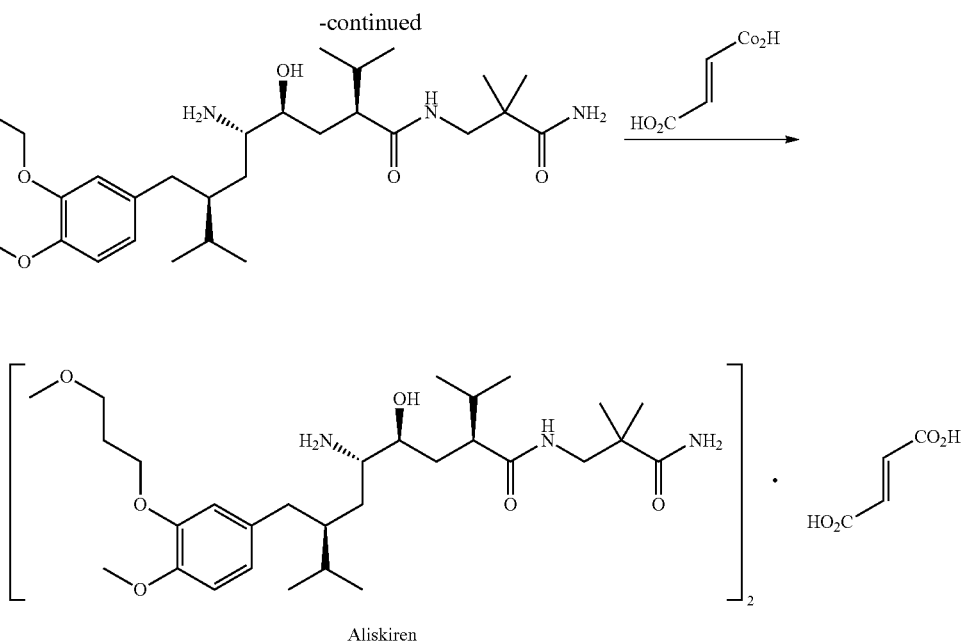

Aliskiren

Two key intermediate compounds I and II are involved in the route.

In U.S. Pat. No. 5,559,111A, the compound I is obtained from compound III, and $Ph_3P$, NBS by controlling the raw materials to react in methylene chloride (solvent) at room temperature for 16 hours, evaporating the solvent, and conducting column chromatography for the residue; the yield is 50%~60%. No other synthetic methods for compound I have been described in any other literatures, except for this method.

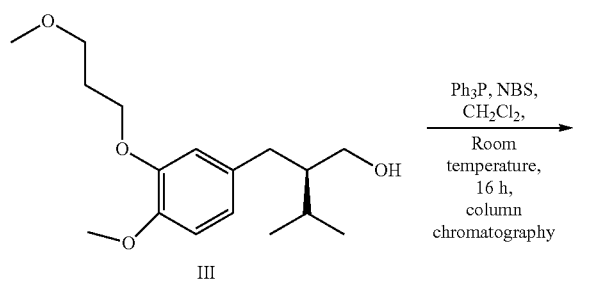

III

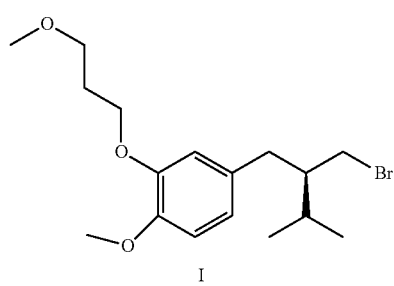

I

In existing literatures (Tetrahedron Letters, 46 (2005), 6337; Helvetica Acta, 86 (2003), 2867), the method for preparation of compound II is as follows:

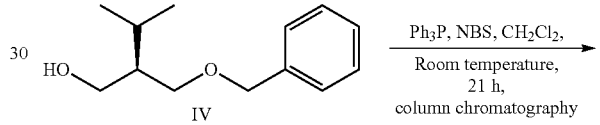

IV

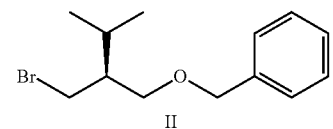

II

The compound II is obtained from compound IV and $Ph_3P$, NBS by controlling the raw materials to react in methylene chloride (solvent) at room temperature for 21 hours, evaporating the solvent, and conducting column chromatography for the residue; the yield is 50%~60%.

The methods for preparation of compounds I and II described above are difficult to be used in industrial production and the yield of the product is low, because the final product has to be separated and purified by column chromatography.

SUMMARY OF THE INVENTION

In view that the methods for synthesizing two key intermediates I and II of Aliskiren in the prior art are difficult to be used in industrial production and the yield of the product is low because the final product has to be separated and purified by column chromatography, the present invention provides a new method for synthesizing the intermediates I and II, which eliminates column chromatography, is easy to be used in industrial production, and can achieve high product purity, and is beneficial for the subsequent grignard reaction to produce a product with higher purity.

The method for synthesizing key intermediates I and II of Aliskiren in the present invention is as follows:

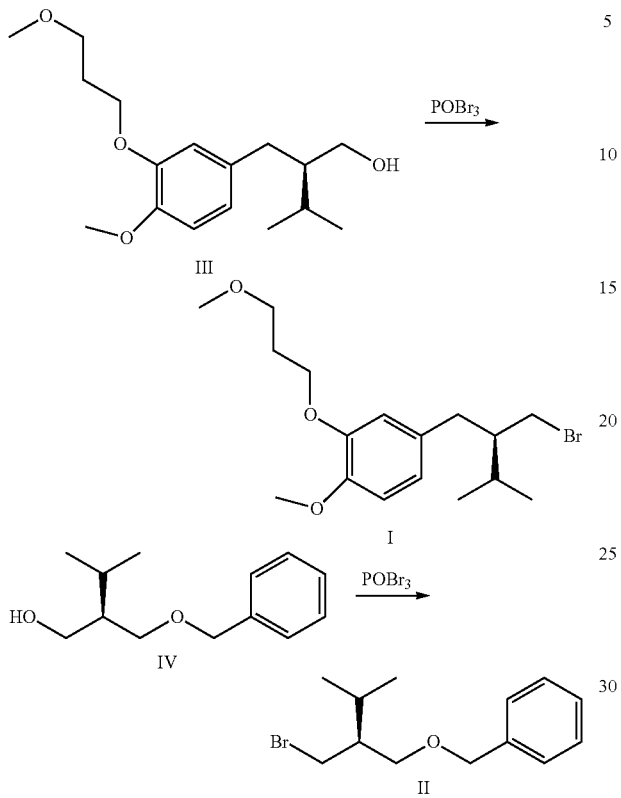

Preferably, the mol ratio of compound III or IV to phosphorus oxybromide is 1:1.0~1:1.2.

The above reaction preferably is conducted in an aprotic solvent. Preferably, the aprotic solvent is ketone, ester, aromatic hydrocarbon, halogenated hydrocarbon, acetonitrile, dimethyl sulfoxide, or N,N-dimethyl formamide, etc. More preferably, the aprotic solvent is methyl benzene, N,N-dimethyl formamide, acetonitrile, methylene chloride, chloroform, ethyl acetate, dimethyl sulfoxide, acetone, or benzene, or a mixture of any two of them. Optimally, the aprotic solvent is methyl benzene and/or N,N-dimethyl formamide.

The reaction temperature is preferably 20~80° C.

The above reaction process further comprises post-treatment of the reactants: adding water in volume equal to 1-3 times of the volume of the reacting solvent into the reactant liquid, extracting with normal hexane or petroleum ether, discarding the aqueous phase, and condensing the organic phase.

The extraction with normal hexane or petroleum ether can be carried out for 1-3 cycles. Preferably, the organic phase is washed with saturated sodium bicarbonate and saturated sodium chloride respectively. Moreover, the organic layer can be dried with anhydrous sodium sulfate.

In the preparation process of compound I, the condensate is preferably recrystallized with an organic solvent after it is dried, and the organic solvent is preferably methanol or a mixed solvent of ethyl acetate/normal hexane.

The compound II can be obtained directly by means of reduced pressure distillation of the condensate.

The preparation method disclosed in the present invention eliminate the column chromatography procedure in the prior art to obtain compounds I and II; the method in the prior art is difficult to be used in mass industrial production; in contrast, the method in the present invention can be used to obtain the product directly by means of recrystallization or reduced pressure distillation, and the obtained product has high chemical purity.

With the method in the prior art, it is difficult for the raw materials III or IV to react completely; therefore, the yield of the product is degraded, and is as low as about 50%~60%; in contrast, with the method disclosed in the present invention, all the raw materials can react completely, and the yield of the product is as high as about 80%.

The product obtained with the method disclosed in the present invention has high chiral purity, and no recemization occurs in the reaction process.

DETAILED DESCRIPTION OF THE EMBODIMENTS

Embodiment 1

Synthesis of (R)-2-[4-methoxy-3-(3-methoxy-propoxy)-benzyl]-3-methyl-butyl bromide Dissolve (R)-2-[4-methoxy-3-(3-methoxy-propoxy)-benzyl]-3-methyl butanol (14.82 g, 50 mmol) in N,N-dimethyl formamide (234 ml), add phosphorus oxybromide (14.33 g, 50 mmol) in droplets slowly and control the temperature at 20° C. in that process, and then let them to react at 20° C. for 8 hours. Cool down to room temperature, and pour the reactant liquid into water (702 ml) slowly, extract with normal hexane for three cycles, combine the normal hexane layers, wash twice with saturated sodium bicarbonate and saturated sodium chloride respectively, dry the organic layer with anhydrous sodium sulfate, filter, and condense the filtrate so as to obtain 17 g of oily matter. Add 51 ml of methanol, control the product to crystallize at −10° C., filter, and then treat the filter cake by vacuum drying at room temperature, so as to obtain 14.3 g of white solid matter; the yield is 79.6%, mp: 51-53° C., chiral purity: ≥99.9%.

$^1$HNMR (ppm, CDCl$_3$): 6.72-6.81 (m, 3H), 4.11 (t, J=6.4 Hz, 2H), 3.84 (s, 3H), 3.58 (t, J=6.4 Hz, 2H), 3.42 (dd, J=4.5, 10.2, 1H), 3.36 (s, 3H), 3.30 (dd, J=4.5, 10.2, 1H), 2.77 (dd, J=4.8, 13.8, 1H), 2.48 (dd, J=4.8, 13.8, 1H), 2.11 (m, 2H), 1.86 (m, 1H), 1.60 (m, 1H), 0.99 (m, 6H).

Embodiment 2

Synthesis of (R)-2-[4-methoxy-3-(3-methoxy-propoxy)-benzyl]-3-methyl-butyl bromide Dissolve (R)-2-[4-methoxy-3-(3-methoxy-propoxy)-benzyl]-3-methyl butanol (14.82 g, 50 mmol) and N,N-dimethyl formamide (0.4 g, 5.5 mmol) in methyl benzene (234 ml), add phosphorus oxybromide (15.05 g, 52.5 mmol) in droplets slowly, and control the temperature below 60° C. in that process; then, let them to react at 80° C. for 2 hours; cool down to room temperature, add water (234 ml), stir for 20 minutes, and separate the layers; extract the aqueous layer with petroleum ether for three cycles, combine the organic layers and wash twice with saturated sodium bicarbonate and saturated sodium chloride respectively; dry the organic layer with anhydrous sodium sulfate, filter, and condense the filtrate so as to obtain 17.2 g of oily matter. Add mixed solvent of ethyl acetate/normal hexane (17.2 ml/34.4 ml), control the product to crystallize at −10° C., filter, and treat the filter cake by vacuum drying at room temperature, so as to obtain 13.5 g of white solid matter; the yield is 75.1%, mp: 51-53° C., chiral purity: ≥99.9%.

Embodiment 3

Synthesis of (S)-2-(benzyloxy-methyl)-3-methyl-butyl bromide

Dissolve (R)-2-(benzyloxy-methyl)-3-methyl butanol (15.6 g, 75 mmol) in N,N-dimethyl formamide (246 ml), add phosphorus oxybromide (22.58 g, 78.75 mmol) in droplets slowly and control the temperature below 50° C. in that process, and then let them to react at 50° C. for 3 hours. Cool down to room temperature, and pour the reactant liquid into water (246 ml) slowly, extract with normal hexane for three cycles, combine the normal hexane layers, wash twice with saturated sodium bicarbonate and saturated sodium chloride respectively, dry the organic layer with anhydrous sodium sulfate, filter, and condense the filtrate so as to obtain 18.1 g of oily matter. Treat the oil matter by reduced pressure distillation to obtain 16.6 g of colorless transparent liquid; the yield is 81.1%, and the chiral purity is ≥99.9%.

$^1$HNMR (ppm, CDCl$_3$): 7.38-7.24 (m, 5H), 4.52 (s, 2H), 3.70 (dd, J=4.4 Hz, 10 Hz, 1H), 3.62 (dd, J=4.4 Hz, 9.6 Hz, 1H), 3.56 (dd, J=5.6 Hz, 10 Hz, 1H), 3.48 (dd, J=7.2 Hz, 9.6 Hz, 1H), 1.84 (m, 1H), 1.70 (s, 1H), 0.97-0.92 (m, 6H).

Embodiment 4

Synthesis of (S)-2-(benzyloxy-methyl)-3-methyl-butyl bromide

Dissolve (R)-2-(benzyloxy-methyl)-3-methyl butanol (15.6 g, 75 mmol) and N,N-dimethyl formamide (0.6 g, 8.25 mmol) in methyl benzene (351 ml), add phosphorus oxybromide (25.8 g, 90 mmol) in droplets slowly, and control the temperature below 60° C. in that process; then, let them to react at 80° C. for 2 hours; cool down to room temperature, add water (702 ml), stir for 20 minutes, and separate the layers; extract the aqueous layer with petroleum ether for three cycles, combine the organic layers and wash twice with saturated sodium bicarbonate and saturated sodium chloride respectively; dry the organic layer with anhydrous sodium sulfate, filter, and condense the filtrate so as to obtain 17.5 g of oily matter; treat the oil matter by reduced pressure distillation to obtain 16.1 g of colorless transparent liquid; the yield is 79.2%, and the chiral purity is ≥99.9%.

The invention claimed is:

1. A method for preparation of a compound I, comprising: preparing by means of reaction between a compound III and phosphorus oxybromide

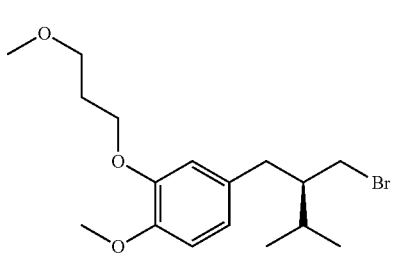

I

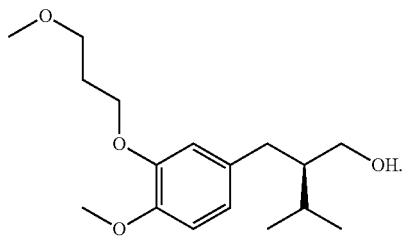

III

2. A method for preparation of a compound II, comprising: preparing by means of reaction between a compound IV and phosphorus oxybromide

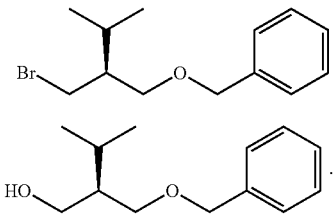

3. The method according to claim 1, wherein, the mol ratio of compound III to phosphorus oxybromide is 1:10~1:1.2.

4. The method according to claim 1, wherein, the reaction is conducted in an aprotic solvent.

5. The method according to claim 4, wherein, the aprotic solvent is selected from methyl benzene, N,N-dimethyl formamide, acetonitrile, methylene chloride, chloroform, ethyl acetate, dimethyl sulfoxide, acetone, or benzene, or a mixture of any two of them.

6. The method according to claim 5, wherein, the aprotic solvent is selected from methyl benzene and/or N,N-dimethyl formamide.

7. The method according to claim 1, wherein, the reaction temperature is 20~80° C.

8. The method according to claim 1, further comprising: after the reaction, adding water into the reactant liquid, extracting with normal hexane or petroleum ether, discarding the aqueous phase, and condensing and drying the organic phase.

9. The method according to claim 8, further comprising: recrystallizing with methanol or a mixed solvent of ethyl acetate/normal hexane.

10. The method according to claim 2, further comprising: after the reaction, adding water into the reactant liquid, extracting with normal hexane or petroleum ether, discarding the aqueous phase, condensing the organic phase, and treating the condensate by reduced pressure distillation.

11. The method according to claim 2, wherein, the mol ratio of compound IV to phosphorus oxybromide is 1:10~1:1.2.

12. The method according to claim 2, wherein, the reaction is conducted in an aprotic solvent.

13. The method according to claim 12, wherein, the aprotic solvent is selected from methyl benzene, N,N-dimethyl formamide, acetonitrile, methylene chloride, chloroform, ethyl acetate, dimethyl sulfoxide, acetone, or benzene, or a mixture of any two of them.

14. The method according to claim 2, wherein, the reaction temperature is 20~80° C.

* * * * *